United States Patent [19]

Gatiss

[11] 4,024,061
[45] May 17, 1977

[54] PULSE DAMPERS FOR LIQUID CHROMATOGRAPHY

[75] Inventor: John William Gatiss, Cambridge, England

[73] Assignee: Pye Limited, Cambridge, England

[22] Filed: Aug. 26, 1975

[21] Appl. No.: 607,783

[30] Foreign Application Priority Data
Sept. 13, 1974 United Kingdom ............ 40067/74

[52] U.S. Cl. .......................... 210/198 C; 210/349; 417/540
[51] Int. Cl.² .......................................... B01D 15/08
[58] Field of Search ...................... 210/198 C, 349; 417/540, 541, 542; 138/26, 30, 31

[56] References Cited

UNITED STATES PATENTS

| 2,317,796 | 4/1943 | Nielebock | 417/540 X |
| 2,592,836 | 4/1952 | Weber | 417/540 X |
| 3,001,367 | 9/1961 | Bartholomew | 417/540 X |
| 3,537,585 | 11/1970 | Waters | 210/349 X |
| 3,934,456 | 1/1976 | Munk | 210/198 C X |

Primary Examiner—John Adee
Attorney, Agent, or Firm—Frank R. Trifari; David R. Treacy

[57] ABSTRACT

In a liquid chromatograph apparatus, a pulse damper consists of a block of solid material almost filling the cavity of the damper, for example a polytetrafluoroethylene block occupying 99% of the volume of the cavity but arranged to move freely therein.

8 Claims, 5 Drawing Figures

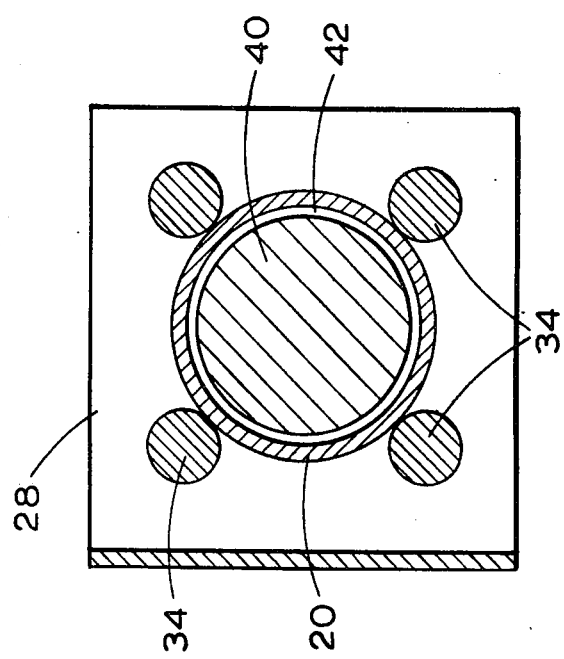
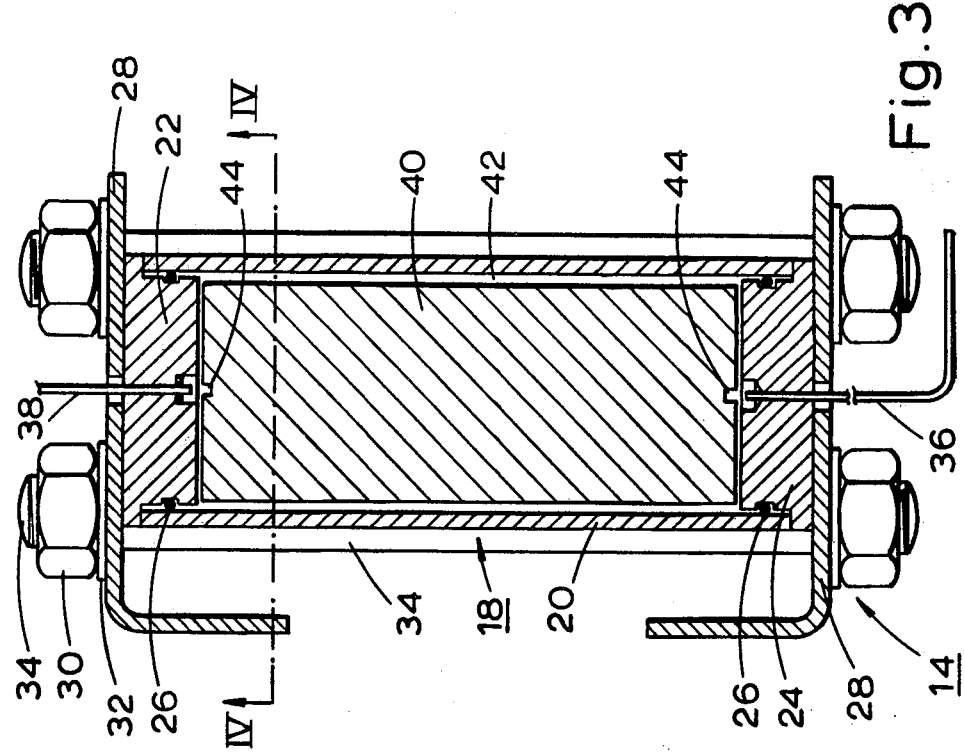

PULSE DAMPERS FOR LIQUID CHROMATOGRAPHY

The invention relates to pulse dampers and to liquid chromatography apparatus including pulse dampers.

In this specification "pulse damper" means a device which reduces fluctuations in pressure in a liquid system. This specification is concerned with pulse dampers which operate by temporarily storing liquid. For example, if a flow of liquid is produced by a reciprocating pump the pulse damper stores liquid during the pumping stroke and releases liquid to the rest of the liquid system during the priming stroke of the pump. The result is to smooth out the pressure (and flow) fluctuations which pass from the pump to the rest of the system. Such pulse dampers have means for allowing a variation in the volume of liquid within them in response to a variation in the pressure of the liquid in the system. Usually a special chamber forms part of the pulse damper. The liquid system of an apparatus may be considered as comprising the vessels, chambers and passages which contain liquid, and the liquid contained in them. The liquid system in a liquid chromatograph apparatus comprises the flow path of liquid in the apparatus and includes any separate pulse damper, the chromatographic column, and any detector through which the liquid flows.

In discussing pulse dampers, the concept of "hydraulic capacitance" may be used. Hydraulic capacitance is analagous to the electrical capacitance, which tends to smooth out changes of current in an electrical circuit. The hydraulic capacitance, $C_h$, of a device or a liquid system which changes its volume by an amount $\Delta v$ for a change in pressure $\Delta p$ may be defined as $C_h = \Delta v/\Delta p$. The capacitance may or may not be constant over a range of pressures.

In ideal terms, if a reciprocating pump is working on a liquid system which consists entirely of restrictive elements (that is to say elements which have no hydraulic capacitance and which are analogous to an electrical resistive impedance), then the pressure in the system, and the volume flow, conveniently may be considered as following the square wave shown in FIG. 1a of the accompanying drawings. In such a system all the components would be quite rigid and the liquid would be incompressible. If some capacitance is introduced in the system, say by means of a pulse damper, then the pressure in the system will be roughly of the form shown in FIG. 1b. The ratio of the pressure ripple $\Delta p$ to the mean pressure $p$ is an indication of the damping in the system. When $\Delta p/p$ approaches zero, the system becomes perfectly damped. The greater the capacitance $C_h$ provided by the pulse damper, the smaller the change in pressure in the system, for a given change in volume of the pulse damper.

In liquid chromatograph apparatus, often a reciprocating pump is used to deliver the solvent or carrier liquid. Reciprocating pumps have various known advantages over other sorts of pumps, particularly for liquid chromatograph systems which operate at relatively high pressure (1000–2000 p.s.i.; 80–160 bar) with low volume flow rates (~1 ml/min). However, reciprocating pumps produce a pulsed liquid supply, and it is known that the presence of pulsations in the pressure or flow of liquid passing to a detector from a liquid chromatograph column can adversely affect the performance of the detector. A pulse damper therefore may be useful in such apparatus.

In one known sort of pulse damper, which may be referred to as a gas accumulator, the rise in pressure in a fluid is alleviated by allowing it to compress a quantity of gas. Gas accumulators are used in applications unconnected with liquid chromatography. We have found that they would have several disadvantages if used in liquid chromatography.

i. Because gases are highly compressible the capacity of gas accumulators is large and there is a large change in volume in the liquid system. Thus if gas accumulators were used in liquid chromatography, a considerable extra amount of liquid would be needed in the liquid system. In liquid chromatography it is desirable to minimise the 'dead volume' in the liquid system, because when the solvent (i.e. the liquid in which the sample is carried through the system) in changed, the components such as pulse dampers often have to be thoroughly flushed through with the new solvent to ensure that none of the old solvent remains. The pump used in high pressure/low flow rate systems may only deliver about 10 ml/min while flushing the system. Thus the desideratum of maximum capacitance has to be tempered by the need to minimise the extra volume introduced in the liquid system by the pulse damper.

ii. In order to avoid excessive alterations in the geometry of the gas enclosure, the gas is usually pre-compressed to just below the working pressure and the working pressure should be reasonably constant. In liquid chromatography the pressure can vary from about 3 to 200 bars (50 to 2000 p.s.i.). This variation cannot be effectively accommodated by a gas accumulator.

iii. Gases approximately obey Boyle's law, so $pv \approx K$. Thus from an initial pressure of $p = 15$ p.s.i., a pressure change $\Delta p = 15$ p.s.i. will cause a volume change $\Delta v$ such that $\Delta v/\Delta p = C_h \approx 2K \times 10^{-3}$. If the initial pressure $p = 50$ p.s.i., the same pressure change $\Delta p = 15$ p.s.i. will cause a volume change such that $C_h \approx 3K \times 10^{-4}$. If the initial pressure $p = 2000$ p.s.i., then over the same pressure change $\Delta p = 15$ p.s.i., $C_h \approx 3K \times 10^{-7}$. It can be seen that the capacitance of a gas accumulator would change by several orders of magnitude over the range of pressures encountered in liquid chromatographic work. Such a change would be too much for a liquid system. There would not be sufficient damping at the higher pressures.

iv. Some sealing membrane is necessary to separate the gas from the liquid in the system. It is difficult to find a material for the membrane which in inert to the liquid in the system. Normally a suitable separating membrane would be a flexible rubber sack containing the gas, but this sort of rubber would not withstand the action of some of the solvents used in liquid chromatography. Moreover a membrane is likely to be to some extent permeable to gas.

v. Generally the sealing membrane has to be flexible to accommodate pressure variations. Continual flexing of the separating membrane would cause fatigue, particularly if it were constructed in some form and material (e.g. stainless steel in the form of bellows, or p.t.f.e.) which were intended to overcome the difficulty mentioned in (iv) above. Liquid chromatographs could be operated continuously for long periods of time (e.g. five years) with the pump probably providing about 100 strokes/min. To avoid failure of the pulse damper, it is necessary to reduce the propensity for fatigue.

vi. The separating material may be rigid. For example it may be a piston slidable in a cylinder between the gas and the liquid. But such an arrangement requires a leak-tight moving seal between the liquid and the gas, which is difficult to achieve.

We have considered a second sort of pulse damper which utilises the stress applied to the walls of the liquid system. For example if a bourdon tube is inserted in the system then as the pressure increases the tube distorts and the increasing stain allows an increase in the volume. However since the wall must be strong enough to withstand the full system pressure safely, it is difficult to provide a large change in volume with pressure, so that the capacitance of the system tends to be small. The greater the capacitance of the system, the more likely it is that the walls be flexing in a manner which in time will cause fatigue problems as mentioned above in connection with the first-mentioned sort of pulse damper.

A known third sort of pulse damper provides in a chamber one or more gas-filled, cellular, foamed or aerated bodies. Such pulse dampers are used in fields of technical application unconnected with liquid chromatography. If applied to liquid chromatography such pulse dampers would have many of the disadvantages listed for the first-mentioned sort of pulse damper. Generally these gas-filled bodies are highly compressible and more suitable for low pressure work. The bodies are often made of foam rubber (e.g. foam rubber balls floating in a chamber in a water system). Such material would not be inert to the solvents used in liquid chromatography. At high pressures the gas would be likely to permeate through the rubber (even if the body were constructed of closed cells) and dissolve in the solvent. An impervious envelope would therefore also be needed. A particularly serious problem would be likely to be the continual flexing of the solid material, which is mentioned above.

It is an object of the invention to provide a pulse damper or a liquid chromatograph including a pulse damper, in which at least some of the above-mentioned difficulties or disadvantages are to some extent alleviated.

According to one aspect of the invention, there is provided a liquid chromatograph apparatus including a pulse damper, the pulse damper comprising one or more entirely solid blocks, which have uniform mechanical properties and construction over all regions, positioned in the liquid system of the apparatus for immersion in the liquid, the volume and the bulk elastic modulus of the one or more blocks being such that the one or more blocks provide a large proportion of the total hydraulic capacitance of the liquid system. The pulse damper may comprise a single said block whose volume and bulk elastic modulus are such that the single block provides said large proportion of the total hydraulic capacitance of the liquid system. The pulse damper may also comprise a chamber connected as part of the liquid system, the block or blocks being contained in the chamber. The bulk elastic modulus of the block or blocks may be of the same order of magnitude as that of the liquid.

According to another aspect of the invention, there is provided a pulse damper to reduce fluctuations in pressure in a liquid system to which it may be connected by temporarily storing liquid, comprising a chamber for containing liquid, at least one passage enabling the chamber to be connected as part of a liquid system, and means allowing a variation in the volume of liquid within the chamber in response to a variation in pressure of the liquid in a liquid system, the said means consisting of one or more entirely solid blocks each of which has substantially uniform mechanical properties and construction over all regions and is contained within the chamber. The said means may consist of a single entirely solid block. The bulk elastic modulus of the block or blocks may be of the same order of magnitude as that of water.

According to either of the above-mentioned aspects of the invention, the block may occupy a large proportion (e.g. 99%) of the total volume of the chamber. The block may be homogeneous and composed of a single material. The block may be composed of a material (e.g. polytetrafluoroethylene) which is chemically inert with respect to liquids normally used in liquid chromatography. The block or blocks may be able to be in contact with liquid over all the surfaces of the block. The block or blocks may be free to move within the chamber. The chamber may be connected, or adapted to be connected, to the liquid system via one passage in the wall of the chamber. There may be a further passage in the wall of the chamber at the opposite end of the chamber from the first, the further passage leading to, or enabling connection to, a drain valve which is normally closed but which when open allows liquid to be passed through the pulse damper from one end to the other. The total volume of the chamber may be approximately 100 ml. The chamber may comprise an open-ended stainless steel tube and stainless steel end plates with a sealing ring between each end plate and the tube, the end plates being secured at the ends of the tubs by means of clamping components under a tension greater than the maximum opposing force which would be produced by a pulse in the liquid system.

FIG. 1 illustrates the hydraulic capacitance.

The invention will be further described by way of example with reference to FIGS. 2, 3, 4 and 5 of the accompanying drawings, in which:

FIGS. 3 and 4 illustrate a pulse damper according to the invention; and

Figure 1:
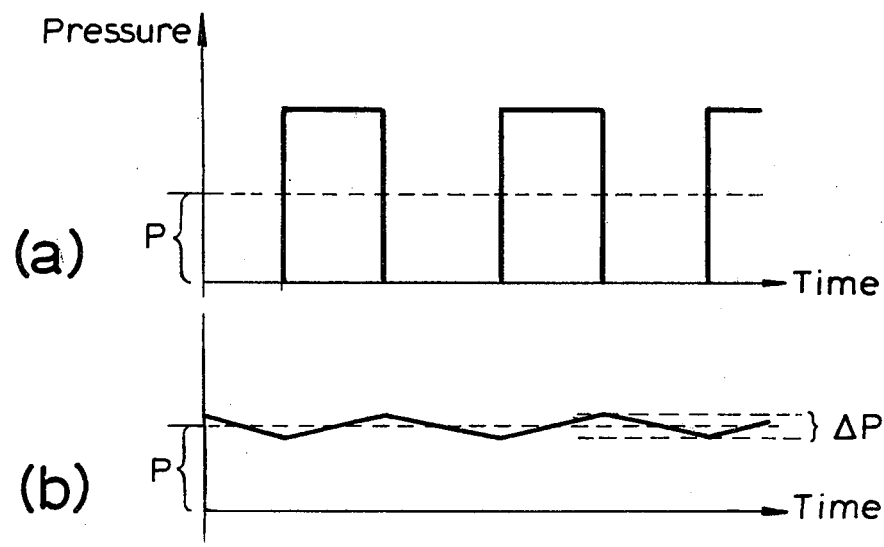
Figure 2:
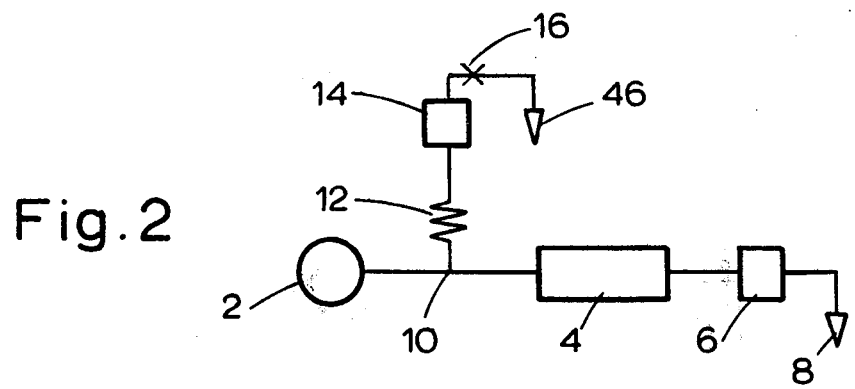
FIG. 2 represents components of a liquid chromatograph apparatus according to the invention.

FIG. 2 schematically illustrates the basic components concerned with a liquid system of a liquid chromatograph apparatus. Other components of the apparatus, not directly concerned with the liquid system, are not represented. A pump 2 delivers carrier liquid, or 'solvent', to the liquid system. The pump is a reciprocating pump and performs about 100 strokes per minute. When flushing the liquid system (e.g. when changing solvents) the pump can deliver about ten millilitres per minute (10 ml/min). During a chromatographic separation the pump may be arranged to deliver between ½ and 5 ml/min. A sample to be separated chromatographically may be inserted into the liquid system, by a known injection means which is not shown, between the pump 2 and a chromatographic column 4. The column is typically about 10–20 cms. long and contains only a small amount (about 1 ml) of carrier liquid within it. Because of the small internal volume and the long narrow passages created by the packing in the column 4, the column provides an effective restrictor to liquid flow, and may be regarded as a 'resistive' impedance to fluid flow. The resistive impedance of all the other components of the liquid system may be neglected in comparison with the column. The solvent carrying the sample is pumped through the column 4, where the components of the sample are separated chromatographically. The eluent from the column surpasses to a detector 6, which usually comprises a cell through which the eluent flows and means for photometrically analysing the eluent. The eluent then passes out of the system to the atomsphere at 8.

Between the pump 2 and the column 4 there is a T-junction 10 leading to an arm which includes a length of 'buffer' tube 12 (whose function will be discussed below), a pulse damper 14 and a drain valve 16.

Each time the pump 2 delivers a quantity of liquid to the liquid system, the pulse damper 14 allows the volume of the system to increase with the accompanying increase of pressure, so that the pulses of pressure are reduced considerably and the fluctuations of pressure and flow passing through the column 4 and detector 6 are small, compared with a system which does not include a pulse damper.

The pulse damper 14 shown in FIGS. 3 and 4 includes a chamber 18 formed by a cylindrical tube 20 and end plates 22, 24. The tube and end-plates are made of austenitic stainless steel so as to be inert to the solvents used in liquid chromatography. They are constructed so as to be almost rigid under the variations of pressure of the liquid in the system. Steel is strong under tensile stress, and in this case the strain produced is very small and well within the elastic limits of the material, so that fatigue due to the pressure cycling is avoided. The passage between the end-plates 22, 24 and the tube 20 are sealed by two standard p.t.f.e. 'O'-rings 26. The end-plates 22, 24 are secured in position by strong end brackets 28 and clamping nuts 30, washers 32 and studs 34. The clamping components are made from mild steel. A predetermined torque is applied to the nuts when the chamber is assembled, such that the clamping studs are permanently under tension. It is arranged that the tension in the studs is in total greater than the maximum force that will be exerted on the end-plates by the liquid under working conditions. Then, since the tube 20 may be regarded as being substantially rigid in comparison with both the liquid and the studs 34, the studs do not experience any effective change in tension or any fluctuating fatigue loading during pressure cycling of the liquid system. For the same reasons, there is effectively no relative motion between the tube 20 and the end-plates 22, 24 so the O-ring seals 26 operate in a truly static condition. These features of the chamber are particularly suitable for a pulse damper is liquid chromatography, as can be seen from the discussion earlier in the specification. A cyclindrical chamber with suitable features might also be constructed in other ways. For example, the end-plates be welded or otherwise secured to the tube, or the chamber might be an integrally-constructed steel cylinder.

A stainless steel tube 36 leads through the end plate 24 to which it is vacuum brazed. The tube 36 is connected to the buffer tube 12 (FIG. 2) and provides a passage which allows working fluid to enter and leave the chamber 18 during pressure cycling. A similar tube 38 through the other end plate 26 is connected to the drain valve 16 (FIG. 2) and provides a passage which enables the liquid to be flushed through the chamber 18 when desired.

Contained within the chamber is an entirely solid, homogeneous block 40 of p.t.f.e. The internal volume of the chamber is 100 ml., and the volume of the p.t.f.e. block is about 99 ml. The p.t.f.e. block 40 is not attached to the walls of the chamber 18 and is surrounded by a thin layer 42 of the liquid. At each end face of the block 40 there is a diametrical channel 44. These channels are provided to allow flow of liquid between the tube 36, 38 at the ends of the chamber even if the block 40 moves up against one of the end-plates 22, 24.

The block allows a variation in the volume of the liquid within the chamber in response to a variation in the pressure of the liquid in the liquid system. We have found that the p.t.f.e. block has a bulk modulus of elasticity which is of the same order of magnitude as water and other liquids used as solvents in liquid chromatography. The hydraulic capacitance of the pulse damper is roughly the same as it would be if the p.t.f.e. block 40 were not present and the chamber were filled only with liquid. However, the total volume of liquid that would be needed to operate a pulse damper consisting of a chamber containing 100 ml. of working liquid would not be acceptable in the field of liquid chromatography, for reasons given elsewhere in the specification. In the present pulse damper, provision of the p.t.f.e. block in the chamber reduces the volume of the liquid in the pulse damper by a factor of about 100.

The particular pulse damper shown in FIGS. 3 and 4 has two advantageous features for liquid chromatography. First, the block is immersed in the liquid, so that the liquid exerts a hydrostatic pressure on it, i.e. exerts a uniform pressure all over the surface of the block. Second, the block is entirely solid, and homogeneous (so that is has substantially uniform mechanical properties, structure and chemical composition throughout the block) so that the hydrostatic pressure on it causes a uniform compression of the block.

In contrast, in general, if an object is subjected to non-uniform pressures on its surface, then tensile and shear stresses are introduced which can result in permanent distortion and/or fatigue failure. Further, if the object is not of homogeneous construction (e.g. is of bellows form, or cellular construction — i.e. is not entirely solid, or has an envelope around a compressible interior, or is of any other composite construction) then tensile and shear forces will occur within the object even when the body is subjected to hydrostatic pressure, and these may result in permanent distortion or fatigue. In principle this applies to any body which is not quite homogeneous and in particular not made of a single material. In practice, a small deviation from this ideal may not materially affect the life of the body. The following conditions should be fulfilled:

i. the material or materials of which the body is formed is or are all solid; (ii) the composition of the body is homogeneous on the macroscale (thus the two materials are uniformly distributed through the body and there are no concentrations of one particular material); (iii) the construction of the body is uniform (for example it does not consist of a shell of one material around an interior of another material). The object might be composed of materials whose bulk moduli of elasticity are very similar. Again, the object might contain a relatively small proportion of a material with a different bulk modulus. For example, in the pulse damper shown in FIGS. 3 and 4 the block could be composed of 10% glass fibre filled p.t.f.e. The capacitance of such a block could be less than a p.t.f.e. block. But because the glass and p.t.f.e. are both solid and the fibres are only about 0.005 inch diameter and are homogeneously distributed through the material, the life of the pulse damper is not likely to be seriously affected.

It can be seen from the foregoing that the pulse damper should comprise an entirely solid block which has uniform mechanical properties and construction over all its regions.

Using p.t.f.e., the limit in the magnitude of the pressure to which the block may be subjected is not likely to be mechanical instability, or deformation. Rather it may be determined by other changes, e.g. chemical changes, which might be induced under high pressures. A device as shown in FIGS. 3 and 4 has been pressure tested up to more than 300 bar without any indication of the occurrence of such effects. In more normal use at pressures up to 160 bar, the device is geometrically stable, is inert to liquid chromatograph solvents, and does not appear to absorb any solvent.

Working the system described with reference to FIGS. 2, 3 and 4 at an average pressure of 80 bar, the pump delivers about 1 ml/min at about 100 strokes/min. (about 10 μl/stroke), and a pressure fluctuation of about 2 bar is observed. This corresponds to a capacitance of about 5 microliters per bar. The capacitance of the system is substantially constant at least up to a mean pressure of 160 bar.

Because of the p.t.f.e. block 40 surrounded by liquid, the pulse damper exhibits a capacitance equivalent to about 100 ml of liquid. The volume of liquid within the pulse damper 14 is about 1 ml. This volume could readily be reduced if more stringent methods were used in manufacturing the components of the pulse damper. The volume of the remainder of the liquid system is about 8 ml. The components which contain the liquid are substantially rigid. Thus the pulse damper provides a large proportion of the total capacitance of the liquid system.

In liquid chromatography it is often necessary to change the solvent in the liquid system. This usually involves purging the system by flushing through relatively large quantities of the new solvent, to ensure that none of the old solvent remains. To purge the pulse damper 14, the drain valve 16, FIG. 2, is opened. Liquid then flows into the pulse damper through the tube 36, through the chamber 18 in the spaces occupied by the thin layer of liquid 42, out of the pulse damper through the tube 38 at the other end of the chamber and past the drain valve 16 to the atmosphere at 46. It has been found that the pulse damper described with reference to FIGS. 3 and 4 can be readily purged of any traces of the old solvent by flushing through a volume of new solvent equal to say ten times the volume of liquid held within the pulse damper. Thus the pulse damper may be purged by flushing through about 10 ml. of the new solvent. At the maximum pump rate of 10 ml/min, the solvent can be changed in about 1 minute. By contrast it can be seen that if the p.t.f.e. block 40 was removed and the chamber 18 ws filled with liquid (as explained above, this would provide approximately the same capacitance), the amount of liquid needed to purge the system might be increased 100-fold. This would clearly be disadvantageous, in practice, in terms of time and of solvent wastage.

The 'buffer' tube 12 shown in FIG. 2, which is an optional component of the system, is a coil of stainless steel capillary tubing, approximately of length 500 m.m., internal diameter 30 thou (.0.75 mm), and external diameter 1/16 inch (1.5 mm). This tube 12 is provided as an additional safeguard to avoid mixing of solvents in the mainstream of the liquid system (i.e. the column 4 and the detector 6) when the solvent has been changed. The volume of liquid within the tube 12 (about 0.2 ml) is greater than the change in internal volume of the pulse damper (approx. 0.1 ml) caused by the changes in the pressure in the liquid system under the normal working conditions. Thus the liquid ejected from the pulse damper 14 when the pressure drops normally does not travel as far as the T-junction 10 and is not entrained in the mainstream of liquid which passes through the column 4 and detector 6. Thus even if traces of the old solvent remain in the thin layer of liquid 42 occupying the space within the pulse damper, these traces are not likely to get into the mainstream.

A technique sometimes used in liquid chromatography is to change the solvent while a chromatographic separation is in progress, by altering the composition of the solvent pumped into the system. The buffer tube is particularly useful when this technique is being used as it reduces the amount of mixing between the liquid in the pulse damper and in the mainstream.

The dimensions of the buffer tube 12 are such that it does not appreciably affect the volume, hydraulic capacitance or 'resistance' of the liquid system.

Figure 5:
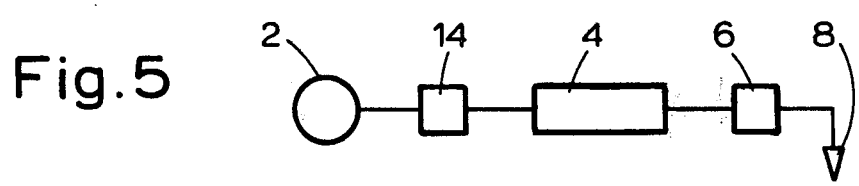
FIG. 5 represents components of another liquid chromatograph apparatus according to the invention.

A pulse damper substantially the same as the pulse damper described with reference to FIGS. 3 and 4 could also be used in a through-flow mode in a liquid system in which the liquid enters through the tube (e.g. 36) at one end and leaves through the tube (e.g. 38) at the other. FIG. 5 represents a liquid system of a chromatograph apparatus where the pulse damper 14 is positioned "in-line" between the pump 2 and the column 4. Similar components to FIG. 2 are indicated by the same reference numerals. The pulse damper in principle could be the same as the damper shown in FIGS. 3 and 4, and would have a similar effect on the pressure and flow variations. It would have a similar pulse damping effect in the system represented in FIG. 5 as in the system represented in FIG. 2. Various modifications of the pulse damper 14 described with reference to FIGS. 3 and 4 are of course possible and may be useful for various applications, although some of the above-mentioned considerations of advantages and drawbacks may need to be borne in mind especially if the system is used for liquid chromatography. For example in principle the block 40 may be replaced by two or more blocks occupying substantially the same space. Such an arrangement would not increase the capacitance and it might be less easy to purge the pulse damper when the solvent is being changed. Again, the block need not be totally free within the chamber (as it is in the pulse damper described with reference to FIGS. 3 and 4): the block could be fixed in position within the chamber, e.g. by a bolt or by adhesive. In such an arrangement however seem would seen preferable for the block to be secured in such a manner that it can respond to changes in the hydrostatic pressure by altering its dimensions uniformly over the whole block, and this would probably require that it is surrounded over all or most of its surface by the liquid.

It has been mentioned above that p.t.f.e. is a suitable material for the block within the chamber of the pulse damper, mainly because it is homogeneous, physically stable, and inert to the solvents used in liquid chromatography. The invention is of course not restricted to the use of p.t.f.e. and other materials, particularly stainless steel, possess the three above-mentioned qualities. Approximate values of the bulk moduli of elasticity of various substances are given below:

| Substance | Bulk modulus |
|---|---|
| | (newtons per square metre) |
| Steel | $17 \times 10^{10}$ |
| Aluminum | $7.5 \times 10^{10}$ |
| Glass | $5 \times 10^{10}$ |
| Water | $3 \times 10^{9}$ |
| Acetone | $2 \times 10^{9}$ |
| Alcohol | $2 \times 10^{9}$ |

The last three substances listed are liquids commonly used as solvents in liquid chromatography. We have found that p.t.f.e. has a bulk modulus of the same order of magnitude as these three liquid substances. The first three substances are other solid substances which might be useful as the compressive element in a pulse damper for liquid chromatography. The bulk moduli of these solid substances however is at least an order of magnitude greater than the bulk modulus that we have found p.t.f.e. to exhibit. Thus if the block 40 (FIG. 3) were made of stainless steel, its volume would need to be between 10 and 100 times as great as the p.t.f.e. block, in order to exhibit the same capacitance as the p.t.f.e. block. Such increased size would in practice be disadvantageous. The volume of liquid surrounding this larger block in the layer 42 probably need not necessarily be greater, since stainless steel could be machined to smaller tolerances. The chamber 18 would not have to withstand any greater pressure than if the block were p.t.f.e., but because of its much greater size the chamber would need to be of stronger construction if it were to withstand this pressure without distorting. Thus we have found it to be advantageous for use in liquid chromatography for the block to be constructed of a material which has a bulk modulus of elasticity of the same order of magnitude as the liquid.

What we claim is:

1. A liquid chromatograph apparatus comprising a liquid system including a pulse damper, said system being arranged to contain a liquid and having an given total hydraulic capacitance, wherein said pulse damper comprises a chamber having rigid walls and enclosing a cavity having a given volume, means for communication of said liquid with said cavity, and at least one block formed entirely of a solid material and arranged to be immersed in said liquid, said at least one block being arranged in said cavity and occupying a large portion of the volume of the cavity, said solid material having a volume and a bulk elastic modulus such that compressibility of said material provides a major portion of the total hydraulic capacitance.

2. An apparatus as claimed in claim 1 wherein said pulse damper comprises one solid block only, said block having uniform mechanical properties and construction over all regions.

3. An apparatus as claimed in claim 2 wherein said block is made of homogeneous material.

4. An apparatus as claimed in claim 3 wherein said material has a bulk elastic modulus of the same order of magnitude as that of said liquid.

5. An apparatus as claimed in claim 2 wherein said material is polytetrafluoroethylene.

6. An apparatus as claimed in claim 1 wherein said proportion is approximately 99%.

7. An apparatus as claimed in claim 1 wherein said block is arranged to be free to move within the chamber.

8. An apparatus as claimed in claim 1 wherein said means for communication comprises a first passage through an end wall of the chamber, said chamber additionally comprising a second passage through the chamber wall at an end opposite said first passage, and means for communicating between said second passage and a drain valve, whereby liquid can be passed through the pulse damper from one end to the other.

* * * * *

UNITED STATES PATENT AND TRADEMARK OFFICE
CERTIFICATE OF CORRECTION

PATENT NO. : 4024061
DATED : May 17, 1977
INVENTOR(S) : John William Gatiss

It is certified that error appears in the above-identified patent and that said Letters Patent are hereby corrected as shown below:

Column 5, line 57, before "be welded" insert --might--